(12) United States Patent
Zhang et al.

(10) Patent No.: US 9,428,539 B2
(45) Date of Patent: Aug. 30, 2016

(54) 2β,3α,5α-TRIHYDROXY-ANDROST-6-ONE AND PREPARATION METHODS AND USE THEREOF

(71) Applicant: Guangzhou Cellprotek Pharmaceutical Co., Ltd., Guangzhou (CN)

(72) Inventors: Jingxia Zhang, Guangzhou (CN); Suizhen Lin, Guangzhou (CN); Minyu Xie, Guangzhou (CN)

(73) Assignee: Guangzhou Cellprotek Pharmaceutical Co., Ltd., Guangzhou (CN)

( * ) Notice: Subject to any disclaimer, the term of this patent is extended or adjusted under 35 U.S.C. 154(b) by 0 days.

(21) Appl. No.: 14/780,464

(22) PCT Filed: Mar. 28, 2014

(86) PCT No.: PCT/CN2014/074318
§ 371 (c)(1),
(2) Date: Sep. 25, 2015

(87) PCT Pub. No.: WO2014/154179
PCT Pub. Date: Oct. 2, 2014

(65) Prior Publication Data
US 2016/0039862 A1    Feb. 11, 2016

(30) Foreign Application Priority Data

Mar. 28, 2013  (CN) .......................... 2013 1 0104162

(51) Int. Cl.
| | | |
|---|---|---|
| *A61K 31/568* | (2006.01) | |
| *C07J 1/00* | (2006.01) | |
| *A61K 45/06* | (2006.01) | |

(52) U.S. Cl.
CPC ............ *C07J 1/0007* (2013.01); *A61K 31/568* (2013.01); *A61K 45/06* (2013.01); *C07J 1/007* (2013.01)

(58) Field of Classification Search
CPC ........................................................ C07J 1/0007
USPC ........................................... 552/614; 514/178
See application file for complete search history.

(56) References Cited

U.S. PATENT DOCUMENTS 8,829,213 B2   9/2014  Peng et al.

FOREIGN PATENT DOCUMENTS

| WO | WO 00/56757 | 9/2000 |
| WO | WO 2011/127465 | 10/2011 |

OTHER PUBLICATIONS

International Search Report and Written Opinion for PCT/CN2014/074318 filed Mar. 28, 2014, mailed Jun. 30, 2014.
International Preliminary Report on Patentability for PCT/CN2014/074318 filed Mar. 28, 2014, mailed Sep. 29, 2015.

*Primary Examiner* — Barbara P Badio
(74) *Attorney, Agent, or Firm* — Sheppard Mullin Richter & Hampton LLP

(57) ABSTRACT

The present invention discloses compound 2β,3α,5α-trihydroxy-androst-6-one, having the structure of formula (I). The present invention also discloses a plurality of methods for preparing the compound and a use of the compound.

Formula (I)

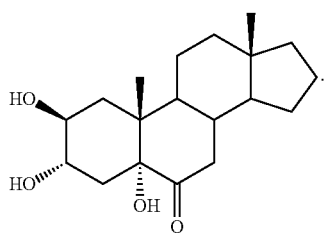

6 Claims, 5 Drawing Sheets

2β,3α,5α-TRIHYDROXY-ANDROST-6-ONE AND PREPARATION METHODS AND USE THEREOF

CROSS-REFERENCE TO RELATED APPLICATION

The present application is a U.S. National Stage Application under 35 U.S.C §371 of International Application No. PCT/CN2014/074318, filed Mar. 28, 2014 which claims priority from Chinese patent application No. 201310104162.5 filed on Mar. 28, 2013, the entire content of which is hereby incorporated herein by reference.

FILED OF THE INVENTION

The present invention relates to a polyhydric sterone, in particular 2β,3α,5α-trihydroxy-androst-6-one, and its preparation methods and medical uses.

BACKGROUND OF THE INVENTION

Polyhydric sterones are a group of important compounds that are widely naturally occurred. Many polyhydric sterones isolated from marine organisms and terrestrial plants have important physiological functions such as antineoplastic and immunity enhancement effects. For example, ecdysterones and brassinosteroids are growth-promoting compounds for plants.

However, naturally occurring polyhydric sterones are contained in plants at an extremely low level, the purification procedures of which are thus complicated and time-consuming. In addition, due to structural complexities for example relatively longer and complicated side chains, most compounds of this group are not synthesizable, which restricts their applications. It will be of great significance with respect to the ranges of applications if those naturally occurring compounds are structurally optimized such that they substantially maintain inherent pharmaceutical properties, while having simplified structures to facilitate synthesis.

SUMMARY OF THE INVENTION

The present invention provides a novel polyhydric sterone, i.e., 2β,3α,5α-trihydroxy-androst-6-one (hereinafter referred to as YC-10, compound (I), compound I, as used interchangeably herein), having the structure of formula (I):

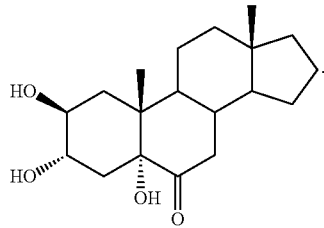

Formula (I)

The compound of formula (I) was synthesized by the present inventors. The compound has relatively simple structure compared to many naturally occurring polyhydric sterones. For example, it does not contain long or complex side chains, allowing for easy synthesis. In addition, reduced molecular weight and relatively simple stereochemical structure are beneficial to drug delivery. Furthermore, the removal of side chains decreases the possibility that the compound interacts with other substances. Moreover, the absence of side chain at 17-position of the compound (I) may improve in vivo bioavailability of the compound and eliminate hormone-like effects thereof. Further, a unique spatial configuration may improve stereoselectivity of the compound, achieving better biological activity.

The compound of formula (I) has proven to posses specific pharmacological effects. In one aspect, the compound is proved to have anti-tumor activity. In another aspect, the compound is proved to have neuron-protective effect, especially for retinal ganglion cells.

Therefore, in one aspect, the present invention provides a pharmaceutical composition comprising therapeutically effective amount of a compound having structure of formula (I), and pharmaceutically acceptable carriers. "Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated. "Pharmaceutically acceptable carriers" refers to a diluent, adjuvant, excipient or carrier with which the compound of the invention is administered.

In another aspect, the present invention provides a pharmaceutical composition comprising therapeutically effective amount of a compound having structure of formula (I), and a second neuron-protective agent. The second neuron-protective agent is different from, but can be used in combination with, the compounds provided by the present invention for neuron-protective purpose. In preferred embodiments, the second neuron-protective agent is an agent protecting retinal ganglion cells.

In a further aspect, the present invention provides a pharmaceutical composition comprising therapeutically effective amount of a compound having structure of formula (I), and a second anti-tumor drug. The second anti-tumor drug is different from, but can be used in combination with, the compounds provided by the present invention for anti-tumor applications.

As used herein, "tumor" means malignant or benign growth of cells in skin or body organs, for example, but not limited to breast, prostate, lung, kidney, pancreas, stomach or intestines. Malignant tumors are prone to invade into adjacent tissues and diffuse (metastasize) to far organs such as bones, liver, lung or brain. The term "tumor" as used herein includes metastatic tumor cell type, for example, but not limited to melanoma, lymphoma, leukemia, fibrosarcoma, leiomyosarcoma and mast cell tumor, and tissue carcinoma type, for example, but not limited to colorectal cancer, prostate cancer, small cell lung cancer and non-small cell lung cancer, breast cancer, pancreatic cancer, bladder cancer, kidney cancer, stomach cancer, glioblastoma, primary hepatic carcinoma, ovarian cancer, prostate cancer and uterine leiomyosarcoma.

In a yet another aspect, the present invention provides a use of a compound having structure of formula (I) in the preparation of neuron-protective medicines or anti-tumor medicines. The compounds provided by the present invention have been demonstrated to inhibit tumor cell growth in a does-dependent manner, together with significant neuron-protective effect.

In a further yet aspect, the present invention provides a method for treating or alleviating a disease or condition such as diseases or conditions related to retinal nerve injury or neuron damage of central nervous system caused by multiple factors, including ophthalmic diseases, such as retinal ischemia, trauma and optic nerve injury resulting from acute or chronic glaucoma, hypertensive retinopathy, diabetic retinal damage, retinal pigment degeneration and maculopathy, and central nervous system diseases, such as stroke, brain injury, spinal injury, Parkinson's disease (PD), Alzheimer's disease (AD), Huntington disease (HD), and amyotrophic lateral sclerosis (ALS). The method comprises administering to a subject therapeutically effective amount of the compound of formula (I), a prodrug or solvate thereof, or the pharmaceutical compositions provided by the present invention.

As used herein, "prodrug" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

In certain instances the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

In a further aspect, a method for preparing the compound of formula (I) is provided. The method uses androst-5-en-3-ol as starting material to obtain compound VI, i.e., 3β-p-toluensulfonyloxy-5α-hydroxy-androst-6-one; Compound VI is then subject to elimination reaction to obtain compound IX, i.e., 5α-hydroxy-androst-2-en-6-one; Compound IX is then subject to oxidation at 2-position double bond and hydrolysis to obtain compound I.

The compound VI can be prepared by a plurality of methods which are exemplified in the following.

(1) Starting material: androst-5-en-3-ol, followed by $H_2O_2$/formic acid oxidation, alkaline hydrolysis, NBS oxidation, and p-toluensulfonyl chloride protection.

Specifically, the method comprises following steps.

(1a) To a reaction flask is added androst-5-en-3-ol and formic acid, and then $H_2O_2$ is added dropwise at low temperature. The reaction mixture is allowed to react for 1 to 2 hours and then heated. To the reaction mixture is added water and stirred to disperse. The mixture is filtered and dried to give compound II as a white solid. The starting material:formic acid:$H_2O_2$ is 1:10~30:0.5~3 (w:v:v);

(1b) To a reaction flask is added alkaline methanol solution and compound II. The reaction mixture is heated at refluxed for 1-2 h, and poured into water to disperse. The mixture is filtered and dried to provide compound III as a white solid. The alkaline methanol solution is selected from a solution of potassium hydroxide, sodium hydroxide or sodium methoxide in methanol. The alkali concentration of the reaction mixture is 2-10%;

(1c) To a reaction flask is added compound III, dioxane and water. NBS is added in batch. The mixture is reacted for 2-4 h, followed by addition of sodium sulfite. The mixture is filtered, washed with water to neutral, and dried to give compound V as a white solid; and (1d) To a reaction flask is added compound V, pyridine and p-toluensulfonyl chloride. The reaction mixture is stirred for 24-36 h at room temperature and then added to icy hydrochloric acid solution. The mixture is filtered, washed with water to neutral, and dried to give compound VI as a white solid.

(2) Starting material: androst-5-en-3-ol, followed by oxidation with m-chloroperoxybenzoic acid, acidolysis, NBS oxidation and p-toluensulfonyl chloride protection.

Specifically, the method comprises following steps.

(2a) To a reaction flask is added androst-5-en-3-ol and $CH_2Cl_2$. m-Chloroperoxybenzoic acid is added in batch while stirring. The mixture is further stirred for 2-5 h in ice bath. After the reaction was completed, the mixture is washed with $Na_2CO_3$, $Na_2SO_3$ and water, dried and concentrated to give compound IV;

(2b) To a reaction flask is added compound IV and acidic acetone aqueous solution and stirred at room temperature for hours. After the reaction was completed, the reaction solution is adjusted to neutral with $Na_2CO_3$ solution. The acetone is removed and residue is extracted with ethyl acetate. The organic layer is collected, dried and concentrated to provide compound III. The acid in the acidic acetone aqueous solution is sulfuric acid or periodic acid. Compound IV:acetone:1N acid is 1:20~30:5~10 (w:v:v);

(2c) To a reaction flask is added compound III, dioxane and water. NBS is added in batch. The mixture is reacted for 2-4 h, followed by addition of sodium sulfite. The mixture is filtered, washed with water to neutral, and dried to give compound V as a white solid; and (2d) To a reaction flask is added compound V, pyridine and p-toluensulfonyl chloride. The reaction mixture is stirred for 24-36 h at room temperature and then added to icy hydrochloric acid solution. The mixture is filtered, washed with water to neutral, and dried to give compound VI as a white solid.

(3) Starting material: androst-5-en-3-ol, followed by p-toluensulfonyl chloride protection, oxidation with m-chloroperoxybenzoic acid, and Jones reagent oxidation.

Specifically, the method comprises following steps.

(3a) To a reaction flask is added androst-5-en-3-ol, anhydrous pyridine and p-toluensulfonyl chloride. The reaction mixture is stirred at room temperature. After the reaction was completed, the mixture is poured into icy hydrochloric acid solution, stirred, filtered, washed with water to neutral, and dried to provide compound VII as a white solid;

(3b) To a reaction flask is added compound VII and dichloromethane, and m-chloroperoxybenzoic acid is added in batch while stirring. The reaction mixture is further stirred in ice bath. After the reaction is complete, the mixture is washed with saturated sodium sulphite solution, sodium carbonate solution and distilled water. The organic layer is collected, dried, concentrated and purified by silica-gel column chromatography, providing compound VIII as a white solid;

(3c) To a reaction flask is added compound VIII and acetone, followed by addition of Jones reagent while stirring. The mixture is allowed to react for hours at room temperature. After the reaction is completed, the mixture is quenched with isopropanol and adjusted to neutral. The mixture is concentrated under reduced pressure to remove acetone, extracted with ethyl acetate, washed, dried, and concentrated to give a pale green solid. The solid is purified by silica-gel column chromatography to provide compound VI as a white solid.

In the methods of the present invention, compound IX is for example prepared as follows. To a reaction flask is added compound VI, DMF, $Li_2CO_3$ and LiBr. The reaction mixture is heated to reflux and poured into icy aqueous hydrochloric acid solution. The mixture is stirred, filtered, washed to neutral, and dried to give compound IX as a white solid. Preferably, compound VI:DMF is 1:3~15(w:v); compound VI: $Li_2CO_3$: LiBr is 1:4~12:4~12(M:M:M).

In the methods of the present invention, compound I can also be prepared from compound IX by methods exemplified as follows.

(1) Compound I is prepared from compound IX by $H_2O_2$/formic acid oxidation and alkaline hydrolysis.

Specifically, the method comprises the following steps.

(1a) To a reaction flask is added compound IX and formic acid, and then $H_2O_2$ is added dropwise at low temperature. The reaction mixture is allowed to react for 1 to 2 hours and then heated. To the reaction mixture is added water and stirred to disperse. The mixture is filtered to obtain a white filter cake. The cake is dried to give compound X as a white solid. The compound X:formic acid:$H_2O_2$ is 1:10~30:0.5~3 (w:v:v);

(1b) To a reaction flask is added alkaline methanol solution and compound X. The reaction mixture is heated at refluxed for 1-2 h, and poured into water to disperse. The mixture is filtered and dried to provide compound of formula (I) as a white solid. The alkaline methanol solution is selected from a solution of potassium hydroxide, sodium hydroxide or sodium methoxide in methanol. The alkali concentration of the reaction mixture is 2-10%.

(2) Compound I is prepared from compound IX by oxidation with m-chloroperoxybenzoic acid and acidolysis. Specifically, the method comprises the following steps.

(2a) To a reaction flask is added compound IX and $CH_2Cl_2$. m-Chloroperoxybenzoic acid is added in batch while stirring. The mixture is further stirred for 2-5 h in ice bath. After the reaction was completed, the mixture is washed with $Na_2CO_3$, $Na_2SO_3$ and water, dried and concentrated to give compound XI;

(2b) To a reaction flask is added compound XI and acidic acetone solution and stirred at room temperature for hours. After the reaction was completed, the reaction solution is adjusted to neutral with $Na_2CO_3$ solution. The acetone is removed and residue is extracted with ethyl acetate. The organic layer is collected, dried and concentrated to provide compound I. The acid in the acidic acetone aqueous solution is sulfuric acid or periodic acid. Compound XI:acetone:1N acid is 1:20~30:5~10 (w:v:v).

DETAILED DESCRIPTION

Figure 1:
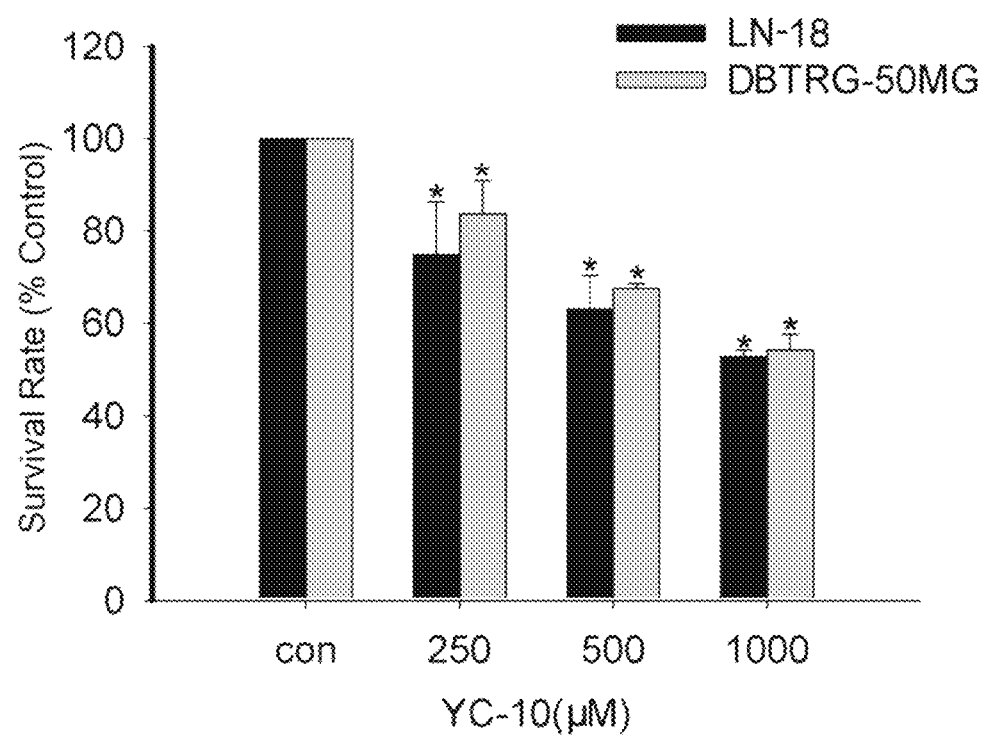
FIG. 1 shows the inhibition of LN18 and DBTRG-50MG cells of compound I of the present invention (n=3*, p<0.05).

The following is provided for illustrative purpose only. It is understood that the scope of the invention shall not be limited to the examples provided below. In the following examples, compound I refers to 2β,3α,5α-trihydroxy-androst-6-one; compound II refers to 3β,6β-diformyloxy-5α-androst-5-ol; compound III refers to androst-3β,5α,6β-triol; compound IV refers to 3β-hydroxy-androst-5β,6β-epoxy; compound V refers to 3β,5α-dihydroxy-androst-6-one; compound VI refers to 3β-p-toluensulfonyloxy-5α-hydroxy-androst-6-one; compound VII refers to 3β-p-toluensulfonyloxy-androst-5-en; compound VIII refers to 3β-p-toluensulfonyloxy-androst-5β,6β-epoxy; compound IX refers to 5α-hydroxy-androst-2-en-6-one; compound X refers to 2β,3α-diformyloxy-5α-hydroxy-androst-6-one; and compound XI refers to 2β,3β-epoxy-5α-hydroxy-androst-6-one.

PREPARATION OF COMPOUND I

Example 1

Step 1—To a 2 L of reaction flask was added compound androst-5-en-3-ol (54.5 g) and formic acid (1 L, 88%). The reaction mixture was cooled to 25° C., and hydrogen peroxide (82.5 mL, 30%) was slowly added. After reaction was completed as evidenced by TLC, the mixture was heated to 75° C. to remove excess hydrogen peroxide. Water (1 L) was added and stirred to disperse. The mixture was filtered to obtain a white filter cake. The cake was immersed into saturated $NaHCO_3$ solution and filtered. Filter cake was washed to neutral and dried to provide compound II (62.4 g) as a white solid.

Step 2—To a 2 L of reaction flask was added potassium hydroxide (45 g), methanol (1500 mL), water (300 mL) and compound II (60 g). The reaction mixture was heated to reflux. TLC confirmed no residual compound II. The reaction mixture was cooled to room temperature, and poured into water (3 L) to disperse. The mixture was adjusted to pH=7 by concentrated hydrochloric acid and allowed for settlement lamination. The mixture was filtered and filter cake was washed to neutral and dried to obtain compound III (49.6 g) as a white solid.

Step 3—To a 1 L of reaction flask was added compound III (49 g), dioxane (600 mL) and water (200 mL). After compound III was completely dissolved, N-bromo-succinimide (42.5 g) was added in four batches. After compound III was depleted as evidenced by TLC, the reaction was stopped. Sodium sulfite (11 g) was added to reduce excess oxidant. The mixture is dispersed in water (4 L) and filtered. Filter cake was washed to neutral and dried to provide compound V (47.8 g) as a white solid.

Step 4—To a 500 mL of reaction flask was added pyridine (135 mL), compound V (44.3 g) and p-toluensulfonyl chloride (45 g). The mixture was stirred at room temperature. After compound V was depleted as evidenced by TLC, the reaction was stopped. The mixture was poured into icy aqueous hydrochloric acid solution (300 mL, 1:1(V:V)), stirred, and filtered. Filter cake was washed to pH=7 and filtered. Filter cake was washed to neutral and dried to provide compound VI (61.7 g) as a white solid.

Step 5—To a 1 L of reaction flask was added N,N-dimethylformamide (325 mL), compound VI (54 g), $Li_2CO_3$ (52.1 g) and LiBr (60.5 g). The mixture is heated to reflux. After compound VI is depleted as evidenced by TLC, the reaction is stopped. The mixture was poured into icy aqueous hydrochloric acid solution (2 L, 1:1(V:V)), stirred and filtered. Filter cake was washed to neutral and dried to provide compound IX (32 g) as a white solid.

Step 6—To a 500 mL of reaction flask was added compound IX (30 g) and formic acid (600 mL, 88%). The mixture was heated to dissolve the solid compound and then cooled to below 25° C. Hydrogen peroxide (24 mL, 30%) was slowly added. After compound IX was depleted as evidenced by TLC, the mixture was heated to 75° C. for 10 minutes to remove excess hydrogen peroxide. Water (3 L) was added and stirred to disperse. The mixture was filtered to obtain a white filter cake. The cake was immersed into saturated $NaHCO_3$ solution and filtered. Filter cake was washed to neutral and dried to provide compound X (26 g) as a white solid.

Step 7—To a 500 mL of reaction flask was added potassium hydroxide (27 g), methanol (600 mL), water (72 mL) and compound X (23.4 g). The reaction mixture was heated to reflux. TLC confirmed no residual compound X. The reaction mixture was cooled to room temperature, and poured into water (3 L) to disperse. The mixture was adjusted to pH=7 by concentrated hydrochloric acid and allowed for settlement lamination. The mixture was filtered and filter cake was washed to neutral, followed by recrystallization in acetone, and dried to obtain compound I (16 g) as a white solid.

m.p:197~201° C.; specific rotation:−50° (2 mg/mL, absolute ethanol); $^1$H NMR($CDCl_3$, 400 MHz)δ:0.65(s, 3H, 18-$CH_3$), 0.87(s, 3H, 19-$CH_3$), 3.76~3.83(d, J=28 Hz, 2H, 2-CH and 3-CH); $^{13}$C NMR($CDCl_3$, 400 MHz)δ: 15.52 ($CH_3$), 17.27($CH_3$), 19.94($CH_2$), 20.53($CH_2$), 24.68($CH_2$), 26.90($CH_2$), 33.02($CH_2$), 36.45(CH), 39.72($CH_2$), 40.92 (C), 41.26($CH_2$), 42.54(C), 44.99(CH), 54.04(CH), 68.94 (CH), 70.19(CH), 79.71(C), 210.65(C); IR(KBr, $cm^{-1}$) v:3296, 2937, 1726, 1064; MS(APCI)m/z: 319(M-3).

PREPARATION OF COMPOUND I

Example 2

Step 1—To a 2 L of reaction flask was added compound androst-5-en-3-ol (70 g) and $CH_2Cl_2$ (1200 mL). To the mixture was added m-chloroperoxybenzoic acid (105 g, mCPBA) in batch while stirring. The reaction mixture is further stirred in ice bath for 5 h. After the reaction was completed, the mixture was washed with saturated sodium sulphite solution, sodium carbonate solution and distilled water. The organic layer was collected, dried, and concentrated to provide compound IV (62 g) as a yellow solid.

Step 2—Compound IV (60 g) was dissolved in acetone (3 L). To the solution was added 1 N $H_2SO_4$ (400 mL) solution. The mixture was stirred at room temperature for 3 h. After the reaction was completed, the mixture was adjusted to neutral with $Na_2CO_3$ solution and concentrated under reduced pressure to remove acetone. The mixture was extracted with ethyl acetate, and organic layer was collected and dried over anhydrous sodium sulfate to give a yellow solid (48 g). The solid was recrystallized in acetone to provide compound III (30.5 g).

Steps 3 to 7 were identical with steps 3 to 7 in Example 1.

m.p:197~201° C.; specific rotation:−50° (2 mg/mL, absolute ethanol); $^1$H NMR($CDCl_3$, 400 MHz)δ:0.65(s, 3H, 18-$CH_3$), 0.87(s, 3H, 19-$CH_3$), 3.76~3.83(d, J=28 Hz, 2H, 2-CH and 3-CH); $^{13}$C NMR($CDCl_3$, 400 MHz)δ:15.52 ($CH_3$), 17.27($CH_3$), 19.94($CH_2$), 20.53($CH_2$), 24.68($CH_2$), 26.90($CH_2$), 33.02($CH_2$), 36.45(CH), 39.72($CH_2$), 40.92 (C), 41.26($CH_2$), 42.54(C), 44.99(CH), 54.04(CH), 68.94 (CH), 70.19(CH), 79.71(C), 210.65(C); IR(KBr, $cm^{-1}$) v:3296, 2937, 1726, 1064; MS(APCI)m/z: 319(M-3).

PREPARATION OF COMPOUND I

Example 3

Steps 1 to 5 were identical to steps 1 to 5 of Example 1.

Step 6—In a 500 mL of reaction flask, compound IX (23 g) was dissolved in $CH_2Cl_2$ (600 mL). To the mixture was added m-chloroperoxybenzoic acid (34.6 g, mCPBA) in batch while stirring. The reaction mixture is further stirred in ice bath for 5 h. After the reaction was completed, the mixture was washed with saturated sodium sulphite solution, sodium carbonate solution and distilled water. The organic layer was collected, dried, and concentrated to provide compound XI (20.7 g) as a yellow solid.

Step 7—In a 2 L of reaction flask, compound XI (17.4 g) was dissolved in acetone (900 mL). To the mixture was added 1 N $H_2SO_4$ solution (180 mL). The mixture was stirred at room temperature for 3 h. After the reaction was completed, the mixture was adjusted to neutral with $Na_2CO_3$ solution and concentrated under reduced pressure to remove acetone. The mixture was extracted with ethyl acetate, and organic layer was collected and dried over anhydrous sodium sulfate to give a yellow solid (14.4 g). The solid was recrystallized in acetone to provide compound I as a white solid.

m.p:197~201° C.; specific rotation:−50° (2 mg/mL, absolute ethanol); $^1$H NMR($CDCl_3$, 400 MHz)δ:0.65(s, 3H, 18-$CH_3$), 0.87(s, 3H, 19-$CH_3$), 3.76~3.83(d, J=28 Hz, 2H, 2-CH and 3-CH);$^{13}$C NMR($CDCl_3$, 400 MHz)δ: 15.52 ($CH_3$), 17.27($CH_3$), 19.94($CH_2$), 20.53($CH_2$), 24.68($CH_2$), 26.90($CH_2$), 33.02($CH_2$), 36.45(CH), 39.72($CH_2$), 40.92 (C), 41.26($CH_2$), 42.54(C), 44.99(CH), 54.04(CH), 68.94 (CH), 70.19(CH), 79.71(C), 210.65(C); IR(KBr, $cm^{-1}$) v:3296, 2937, 1726, 1064; MS(APCI)m/z: 319(M-3).

PREPARATION OF COMPOUND I

Example 4

Step 1—To a 250 mL of reaction flask was added androst-5-en-3-ol (14.64 g) and anhydrous pyridine (125 mL). To the mixture was added in batch p-toluensulfonyl chloride (26.05 g). The mixture was allowed to react at room temperature for 24 h. After starting materials were depleted as evidenced by TLC, the reaction was stopped. The mixture was poured into icy HCl solution (2000 mL, 17%) under vigorous stirring, and filtered. Filter cake was washed to neutral and dried under vacuum to provide compound VII (22.48 g) as a white solid.

Step 2—To a 250 mL of reaction flask was added compound VII (15.00 g) and $CH_2Cl_2$ (200 mL). To the mixture was added m-chloroperoxybenzoic acid (15.12 g, mCPBA) in batch while stirring. The reaction mixture is further stirred in ice bath for 5 h. After the reaction was completed, the mixture was washed with saturated sodium sulphite solution, sodium carbonate solution and distilled water. The organic layer was collected and dried over anhydrous sodium sulfate. Organic solvents were evaporated. The residue was dried under vacuum to provide crude product (14.07 g). The crude product was purified by silica-gel column chromatography to provide compound VIII (12.3 g) as a white solid.

Step 3—To a 1000 mL of reaction flask was added compound VIII (14.07 g) and acetone (750 mL). To the mixture was added Jones reagent (30 mL) while stirring. The mixture was allowed to react at room temperature for 2 h. After the reaction was completed as evidenced by TLC, the mixture is quenched with isopropanol and adjusted to neutral with $Na_2CO_3$ solution. The mixture is concentrated under reduced pressure to remove acetone, and extracted with ethyl acetate. The organic layer was collected and washed with distilled water several times, dried over anhydrous sodium sulfate, and concentrated to give a pale green solid. The solid is purified by silica-gel column chromatography to provide compound VI (12.89 g) as a white solid.

Steps 4 to 6 were identical to steps 5 to 7 of Example 1.

m.p:197~201° C.; specific rotation:−50° (2 mg/mL, absolute ethanol); $^1H$ NMR($CDCl_3$, 400 MHz)δ:0.65(s, 3H, 18-$CH_3$), 0.87(s, 3H, 19-$CH_3$), 3.76~3.83(d, J=28 Hz, 2H, 2-CH and 3-CH);$^{13}C$ NMR($CDCl_3$, 400 MHz)δ: 15.52 ($CH_3$), 17.27($CH_3$), 19.94($CH_2$), 20.53($CH_2$), 24.68($CH_2$), 26.90($CH_2$), 33.02($CH_2$), 36.45(CH), 39.72($CH_2$), 40.92 (C), 41.26($CH_2$), 42.54(C), 44.99(CH), 54.04(CH), 68.94 (CH), 70.19(CH), 79.71(C), 210.65(C); IR(KBr, $cm^{-1}$) v:3296, 2937, 1726, 1064; MS(APCI)m/z: 319(M-3).

PREPARATION OF COMPOUND I

Example 5

Steps 1 to 4 were identical to steps 1 to 4 in Example 1.

Step 5—To a 1 L of reaction flask was added anhydrous N,N-dimethylformamide (325 mL), compound VI (54 g), dry $Li_2CO_3$ (69.5 g), and LiBr (80.6 g). The mixture was heated to reflux. After the compound VI was consumed as evidenced by TLC, the reaction was stopped. The mixture was added to icy HCl aqueous solution (2 L, 1:1 (V:V)), stirred, and filtered. Filter cake was washed with water to neutral and dried to provide compound IX (32.5 g) as a white solid.

Steps 6 to 7 were identical to steps 6 to 7 in Example 1.

m.p:197~201° C.; specific rotation:−50° (2 mg/mL, absolute ethanol); $^1H$ NMR($CDCl_3$, 400 MHz)δ:0.65 (s, 3H, 18-$CH_3$), 0.87(s, 3H, 19-$CH_3$), 3.76~3.83(d, J=28 Hz, 2H, 2-CH and 3-CH);$^{13}C$ NMR($CDCl_3$, 400 MHz)δ: 15.52 ($CH_3$), 17.27($CH_3$), 19.94($CH_2$), 20.53($CH_2$), 24.68($CH_2$), 26.90($CH_2$), 33.02($CH_2$), 36.45(CH), 39.72($CH_2$), 40.92 (C), 41.26($CH_2$), 42.54(C), 44.99(CH), 54.04(CH), 68.94 (CH), 70.19(CH), 79.71(C), 210.65(C); IR(KBr, $cm^{-1}$) v:3296, 2937, 1726, 1064; MS(APCI)m/z: 319(M-3).

PREPARATION OF COMPOUND I

Example 6

Steps 1 to 4 were identical to steps 1 to 4 in Example 1.

Step 5—To a 1 L of reaction flask was added anhydrous N,N-dimethylformamide (325 mL), compound VI (54 g), dry $Li_2CO_3$ (34.7 g), and LiBr (40.3 g). The mixture was heated to reflux. After the compound VI was consumed as evidenced by TLC, the reaction was stopped. The mixture was added to icy HCl aqueous solution (2 L, 1:1(V:V)), stirred, and filtered. Filter cake was washed with water to neutral and dried to provide compound IX (30.2 g) as a white solid.

Steps 6 to 7 were identical to steps 6 to 7 in Example 1.

m.p:197~201° C.; specific rotation:−50° (2 mg/mL, absolute ethanol); $^1H$ NMR($CDCl_3$, 400 MHz)δ:0.65 (s, 3H, 18-$CH_3$), 0.87(s, 3H, 19-$CH_3$), 3.76~3.83(d, J=28 Hz, 2H, 2-CH and 3-CH);$^{13}C$ NMR($CDCl_3$, 400 MHz)δ: 15.52 ($CH_3$), 17.27($CH_3$), 19.94($CH_2$), 20.53($CH_2$), 24.68($CH_2$), 26.90($CH_2$), 33.02($CH_2$), 36.45(CH), 39.72($CH_2$), 40.92 (C), 41.26($CH_2$), 42.54(C), 44.99(CH), 54.04(CH), 68.94 (CH), 70.19(CH), 79.71(C), 210.65(C); IR(KBr, $cm^{-1}$) v:3296, 2937, 1726, 1064; MS(APCI)m/z: 319(M-3).

PREPARATION OF COMPOUND I

Example 7

Steps 1 to 4 were identical to steps 1 to 4 in Example 1.

Step 5—To a 1 L of reaction flask was added anhydrous N,N-dimethylformamide (432 mL), compound VI (54 g), dry $Li_2CO_3$ (52.1 g), and LiBr (60.5 g). The mixture was heated to reflux. After the compound VI was consumed as evidenced by TLC, the reaction was stopped. The mixture was added to icy HCl aqueous solution (2 L, 1:1(V:V)), stirred, and filtered. Filter cake was washed with water to neutral and dried to provide compound IX (30.5 g) as a white solid.

Step 6—To a 500 mL of reaction flask was added compound IX (30 g) and formic acid (600 mL, 88%). The mixture was heated to dissolve the solid compound and then cooled to below 25° C. Hydrogen peroxide (20 mL, 30%) was slowly added. After compound IX was depleted as evidenced by TLC, the mixture was heated to 75° C. for 10 minutes to remove excess hydrogen peroxide. Water (3 L) was added and stirred to disperse. The mixture was filtered to obtain a white filter cake. The cake was immersed into saturated $NaHCO_3$ solution and filtered. Filter cake was washed to neutral and dried to provide compound X (28 g) as a white solid.

Step 7—To a 500 mL of reaction flask was added potassium hydroxide (18 g), methanol (600 mL), water (72 mL) and compound X (25 g). The reaction mixture was heated to reflux. TLC confirmed no residual compound X. The reaction mixture was cooled to room temperature, and poured into water (3 L) to disperse. The mixture was adjusted to pH=7 by concentrated hydrochloric acid and allowed for settlement lamination. The mixture was filtered and filter cake was washed to neutral, followed by recrystallization in acetone, and dried to obtain compound I (8.8 g) as a white solid.

m.p:197~201° C.; specific rotation:−50° (2 mg/mL, absolute ethanol); $^1H$ NMR($CDCl_3$, 400 MHz)δ:0.65 (s, 3H, 18-$CH_3$), 0.87(s, 3H, 19-$CH_3$), 3.76~3.83(d, J=28 Hz, 2H, 2-CH and 3-CH);$^{13}C$ NMR($CDCl_3$, 400 MHz)δ: 15.52 ($CH_3$), 17.27($CH_3$), 19.94($CH_2$), 20.53($CH_2$), 24.68($CH_2$), 26.90($CH_2$), 33.02($CH_2$), 36.45(CH), 39.72($CH_2$), 40.92 (C), 41.26($CH_2$), 42.54(C), 44.99(CH), 54.04(CH), 68.94 (CH), 70.19(CH), 79.71(C), 210.65(C); IR(KBr, $cm^{-1}$) v:3296, 2937, 1726, 1064; MS(APCI)m/z: 319(M-3).

PREPARATION OF COMPOUND I

Example 8

Steps 1 to 5 were identical to steps 1 to 5 in Example 7.

Step 6—To a 500 mL of reaction flask was added compound IX (30 g) and formic acid (600 mL, 88%). The mixture was heated to dissolve the solid compound and then cooled to below 25° C. Hydrogen peroxide (36 mL, 30%) was slowly added. After compound IX was depleted as evidenced by TLC, the mixture was heated to 75° C. for 10 minutes to remove excess hydrogen peroxide. Water (3 L) was added and stirred to disperse. The mixture was filtered to obtain a white filter cake. The cake was immersed into saturated NaHCO$_3$ solution until free of bubbles and then filtered. Filter cake was washed to neutral and dried to provide compound X (24 g) as a white solid.

Step 7 is identical to step 7 in Example 7.

m.p:197~201° C.; specific rotation:−50° (2 mg/mL, absolute ethanol); $^1$H NMR(CDCl$_3$, 400 MHz)δ:0.65 (s, 3H, 18-CH$_3$), 0.87(s, 3H, 19-CH$_3$), 3.76~3.83(d, J=28 Hz, 2H, 2-CH and 3-CH);$^{13}$C NMR(CDCl$_3$, 400 MHz)δ: 15.52 (CH$_3$), 17.27(CH$_3$), 19.94(CH$_2$), 20.53(CH$_2$), 24.68(CH$_2$), 26.90(CH$_2$), 33.02(CH$_2$), 36.45(CH), 39.72(CH$_2$), 40.92 (C), 41.26(CH$_2$), 42.54(C), 44.99(CH), 54.04(CH), 68.94 (CH), 70.19(CH), 79.71(C), 210.65(C); IR(KBr, cm$^{-1}$) v:3296, 2937, 1726, 1064; MS(APCI)m/z: 319(M-3).

PREPARATION OF COMPOUND I

Example 9

Steps 1 to 5 were identical to steps 1 to 5 in Example 7.

Step 6—To a 500 mL of reaction flask was added compound IX (30 g) and formic acid (600 mL, 88%). The mixture was heated to dissolve the solid compound and then cooled to below 25° C. Hydrogen peroxide (45 mL, 30%) was slowly added. After compound IX was depleted as evidenced by TLC, the mixture was heated to 75° C. for 10 minutes to remove excess hydrogen peroxide. Water (3 L) was added and stirred to disperse. The mixture was filtered to obtain a white filter cake. The cake was immersed into saturated NaHCO$_3$ solution until free of bubbles and then filtered. Filter cake was washed to neutral and dried to provide compound X (23 g) as a white solid.

Step 7—To a 500 mL of reaction flask was added potassium hydroxide (27 g), methanol (300 mL), water (36 mL) and compound X (12.5 g). The reaction mixture was heated to reflux. TLC confirmed no residual compound X. The reaction mixture was cooled to room temperature, and poured into water (3 L) to disperse. The mixture was adjusted to pH=7 by HCl and allowed for settlement lamination. The mixture was filtered and filter cake was washed to neutral, followed by recrystallization in acetone, and dried to obtain compound I (8.0 g) as a white solid.

m.p:197~201° C.; specific rotation:−50° (2 mg/mL, absolute ethanol); $^1$H NMR(CDCl$_3$, 400 MHz)δ:0.65(s, 3H, 18-CH$_3$), 0.87(s, 3H, 19-CH$_3$), 3.76~3.83(d, J=28 Hz, 2H, 2-CH and 3-CH);$^{13}$C NMR(CDCl$_3$, 400 MHz)δ: 15.52 (CH$_3$), 17.27(CH$_3$), 19.94(CH$_2$), 20.53(CH$_2$), 24.68(CH$_2$), 26.90(CH$_2$), 33.02(CH$_2$), 36.45(CH), 39.72(CH$_2$), 40.92 (C), 41.26(CH$_2$), 42.54(C), 44.99(CH), 54.04(CH), 68.94 (CH), 70.19(CH), 79.71(C), 210.65(C); IR(KBr, cm$^{-1}$) v:3296, 2937, 1726, 1064; MS(APCI)m/z: 319(M-3).

Anti-Tumor Activity of Compound I

Cell seeding and treatment: Logarithmic phase of LN18 and DBTRG-50MG cells were prepared to cell suspensions with complete medium. Cells were seeded into a 96-well plate at a density of 100 μl per well, 3×10$^4$/ml. 12 h post seeding, full cell adherence was observed. To the wells was added YC-10 to a final concentration of YC-10 being 250, 500, and 1000 μM, with each concentration group having 5 repeats.

Reaction of MTT with succinate dehydrogenase: At 24th h of culturing, 10 μl (5 mg/ml) of MTT was added to each well, followed by 4 h incubation. At this time, granulate violet formazan crystalline can be observed in live cells by microscopy.

Formazan particle dissolution: Supernatant was carefully discharged. To the wells was added DMSO at 100 μl/well to dissolve the crystalline. The mixture was vibrated on a mini oscillator for 5 min and measured for optical density (OD value) at 570 nm for each well by enzyme-linked immunometric assay.

Each group of experiments was repeated 3 times.

Survival (%)=OD value in treatment group/OD value in control group*100%.

All data was presented as mean±SD. SPSS 13.0 statistics package software was used. One-Way ANOVA and t-test were used to analyze the data. Sigmaplot software was used to give FIG. 1. As can be seen from FIG. 1, 24 h post treatment with 250, 500, 1000 μM of YC-10, cell survival rates of treatment group were statistically significant in comparison with control group (P<0.05). YC-10 killed tumor cells in a dose-dependent manner.

Neuron Protective Activity of Compound I

The in vivo and in vitro toxicity and pharmacological functions of YC-10 were studied to evaluate its neuron protective activity and possibility to become potential clinical drug. In summary, results showed that no obvious abnormality was observed in mice administered large doses of YC-10 (250 mg/kg). Studies showed YC-10 was significantly effective in improvement of survival rate of cerebellar granule neurons in both glutamate-induced and low potassium induced injury models. YC-10 was also shown to significantly improve survival rate of retinal ganglion cells in an animal model suffering from both optic nerve injury and retinal ischemia. Those results showed that YC-10 had neuron protective activity, without obvious toxic or side effects.

1 Toxicological Study

Maximal Tolerance Dose Test

YC-10 injections at concentration of 25 mg/mL were prepared with 40% hydroxypropyl cyclodextrin, and were injected through tail vein to 30 KM mice (half males and half females, weighted 18-22 g) at does of 0.1 mL/10 g.

The mice were continuously observed. All mice behaved and ate as usual, with bright coat color and fine fur. No abnormal secretions in mouth, eyes, nose, or ears were observed. Mice defecated normally. Mice weights were slighted increase. No mice died. Mice were sacrificed after 14 days, dissected and visual examined on important organs such as heart, liver, spleen, kidney, and gastrointestinal. No abnormal changes were observed. Those results showed that YC-10 was nontoxic to mouse at 250 mg/kg.

Figure 2:
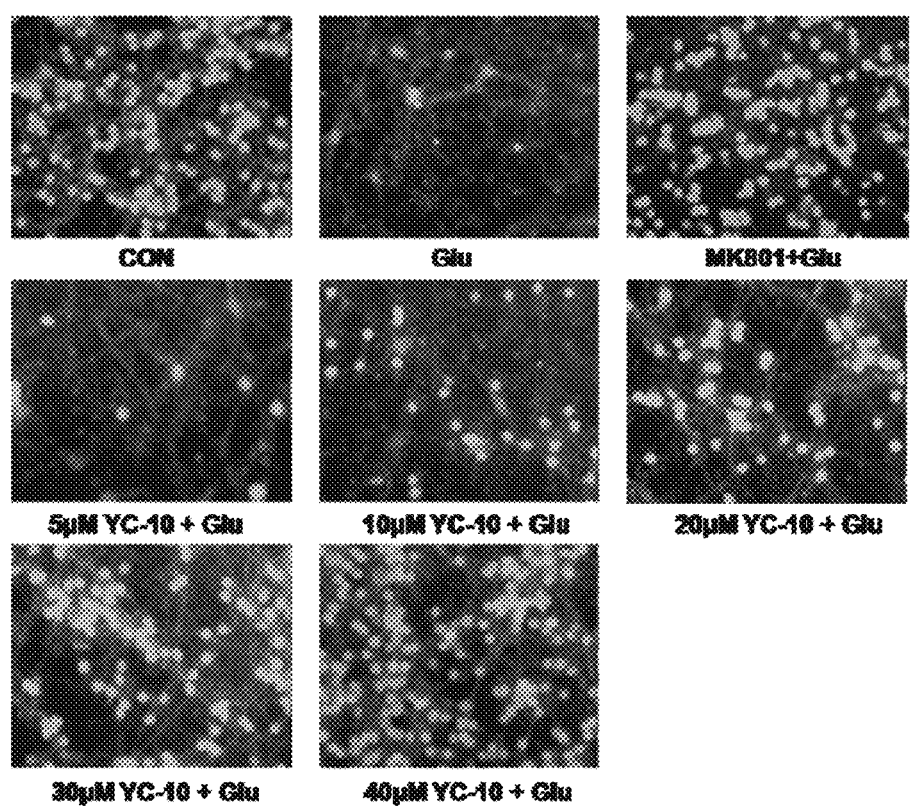
FIG. 2 shows compound I protects cerebellar granule neurons from glutamate-induced damage.

2 Pharmacological Studies 2.1 YC-10 Protected Cerebellar Granule Neurons from Glutamate-Induced Damage Cerebellar granule neurons cultured in vitro for 8 days were grouped. Treatment groups received MK801 or YC-10 at various concentrations, followed by incubation for 30 min. Following that, model group and all treatment groups were replaced with Mg$^{2+}$-free Locke buffer, and added with glutamate (100 μM final concentration), Glycine (10 μM final concentration) and drugs at respective concentrations. Cells were incubated at 37° C. for 30 minutes, replaced with original medium, incubated for further 24 h, followed by FDA staining. Results were shown in FIG. 2.

Figure 3:
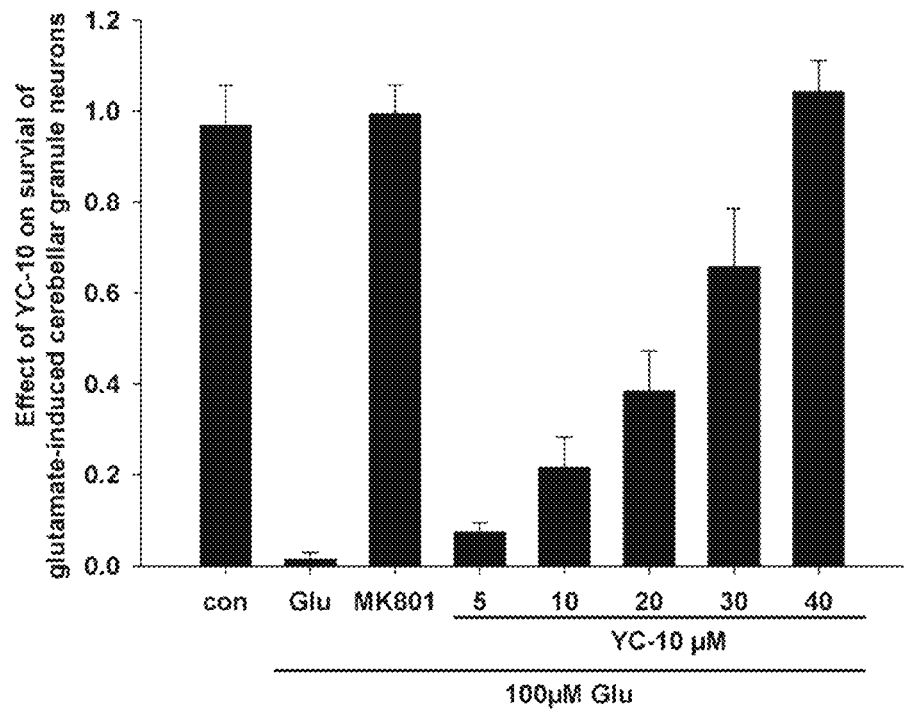
FIG. 3 shows that compound I improves survival of cerebellar granule neurons in a dose-dependent manner.

The results showed that glutamate can induce injury and death of cerebella granule neurons. MK801 was able to prevent cerebella granule neurons from glutamate-induced injury. YC-10 was also effective in preventing glutamate-induced excitotoxin damage of cerebellar granule neurons in a dose-dependent manner. YC-10 protected cerebellar granule neurons against glutamate-induced damage (FIG. 3).

2.2 YC-10 Protected Cerebellar Granule Neurons from Low Potassium-Induced Death

Cerebellar granule neurons were cultured in vitro for 8 days. Treatment groups received YC-10 at various concentrations and incubated for 30 min. Following that, model group and all treatment groups were replaced with 5K (i.e., 5 mM KCl) BME medium (25K BME for control group), and added with YC-10 at respective concentrations. Cells were incubated at 37° C. for 24 h, followed by FDA staining. Results were shown in FIG. 4.

Figure 4:
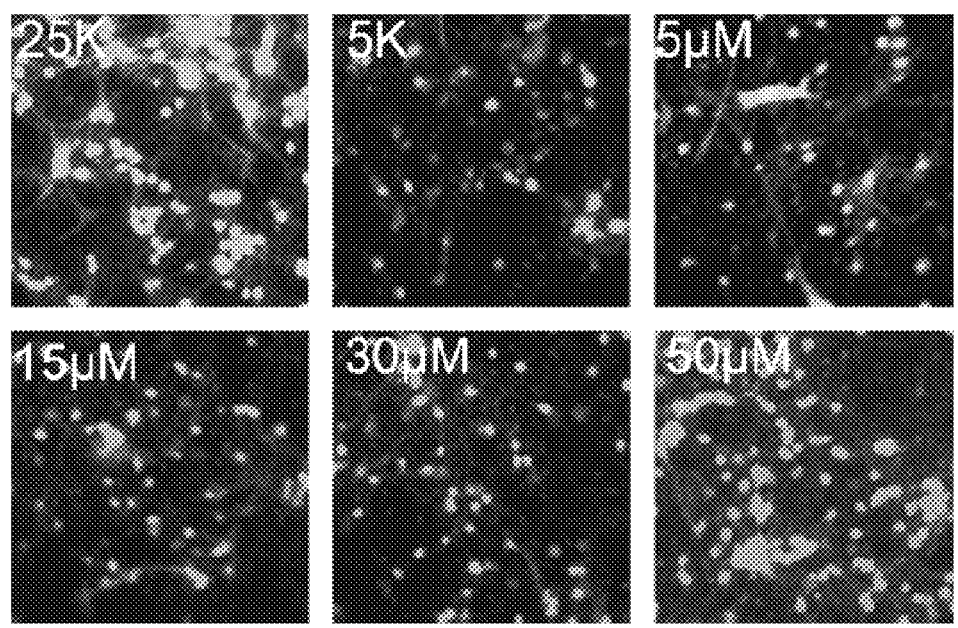
FIG. 4 shows compound I protects cerebellar granule neurons from low potassium induced death.

As shown in FIG. 4, low potassium medium can reduce death of cerebellar granule neurons. YC-10 (50 μM) could prevent neuron from low potassium-induced death. YC-10 protected cerebellar granule neurons from low potassium-induced death.

Figure 5:
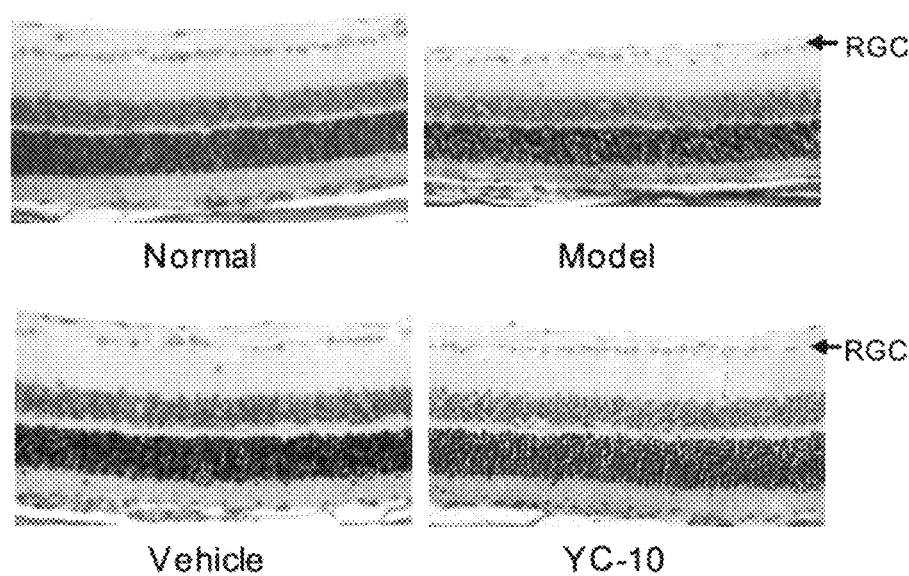
FIG. 5 shows that RGC is significantly decreased in an optic nerve clamping injury model, while compound I is shown to prevent from RGC decrease.
Figure 6:
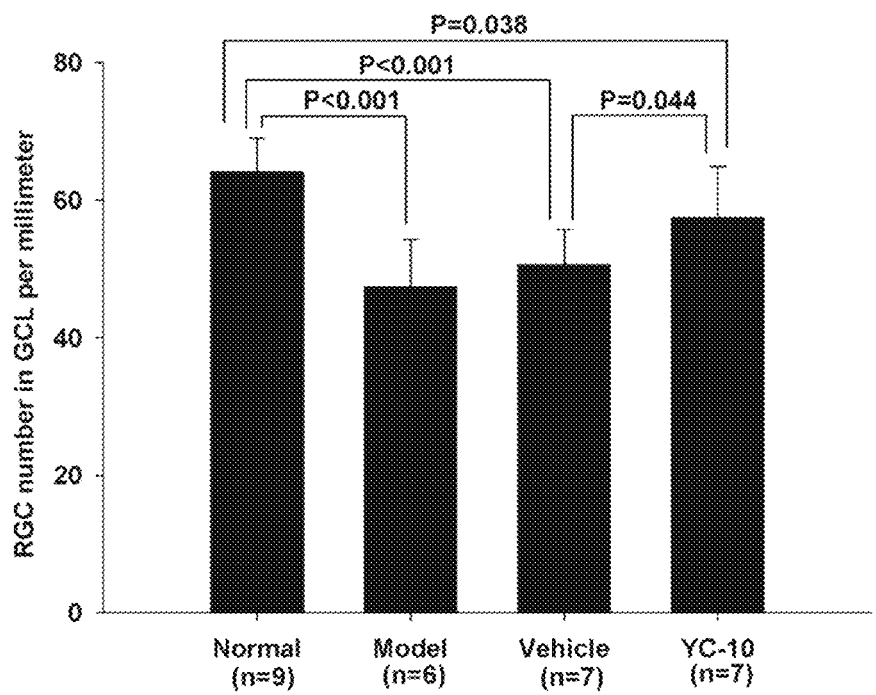
FIG. 6 is a graph showing RGC statistics in different groups of samples in an optic nerve clamping injury model.

2.3 YC-10 Protected Retinal Ganglion Cell from Optic Nerve Clamping Injury-Induced Death 10% chloral hydrate was used to anesthetize rats. YC-10 (20 mg/kg) or solvents were administered via tail vein 20 min before surgery. Eyes were subject to topical anesthesia. Conjunctiva was cut along limbus cornea with corneal scissors and intraocular microforceps. Lateral rectus was bluntly dissected to fully expose optic nerve. A cross action forceps was used to clamp the optic nerve for 5 seconds at 2 mm posterior to the eyeball, and then released. Antibiotic eye ointment was applied post operation to prevent infection. Drugs were administered at 2 h post operation, Day 2, and Day 3. Eyeballs were obtained for pathological examination at Day 7. As shown in FIG. 5, pathological examination showed that optic nerve clamping injury can induce death of retinal ganglion cell (RGC). YC-10 was shown to slow down or prevent from clamping injury-induced death, i.e., YC-10 can protect retinal ganglion cell from optic nerve clamping injury-induced death. RGC counts in each group were recorded and reported in FIG. 6.

2.4 YC-10 Protected Retinal Ganglion Cell from Eye High Pressure and Ischemia Injury-Induced Death 10% chloral hydrate was used to anesthetize rats. Eyes were subject to topical anesthesia. Perfusion apparatus was placed 176 cm above rats' eyeballs (resulting in 130 mmHg intra-ocular pressure). 30 G ½ syringe needle was carefully inserted into anterior chamber. The eyeballs became white and starting time of ischemia was recorded. 1 h post ischemia, the syringe needle was quickly withdrawn and eyes were cared by antibiotic eyedrops. Rats were raised back to cage. Drugs were administered 20 before modeling for solvent group and YC-10 group (20 mg/kg). At 2 h, Day 2 and Day 3 post modeling, rats were treated with YC-10 via tail vein. At Day 7 post modeling, eyeballs were obtained for pathological examination.

Figure 7:
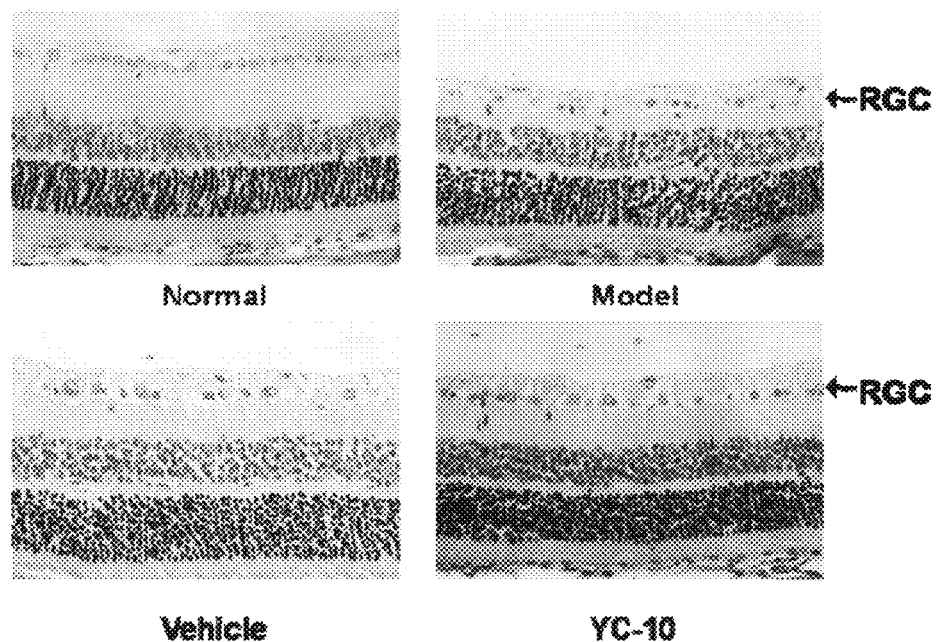
FIG. 7 shows that RGC is significantly decreased in an eye high pressure and ischemia model, while compound I is shown to prevent from RGC decrease.
Figure 8:
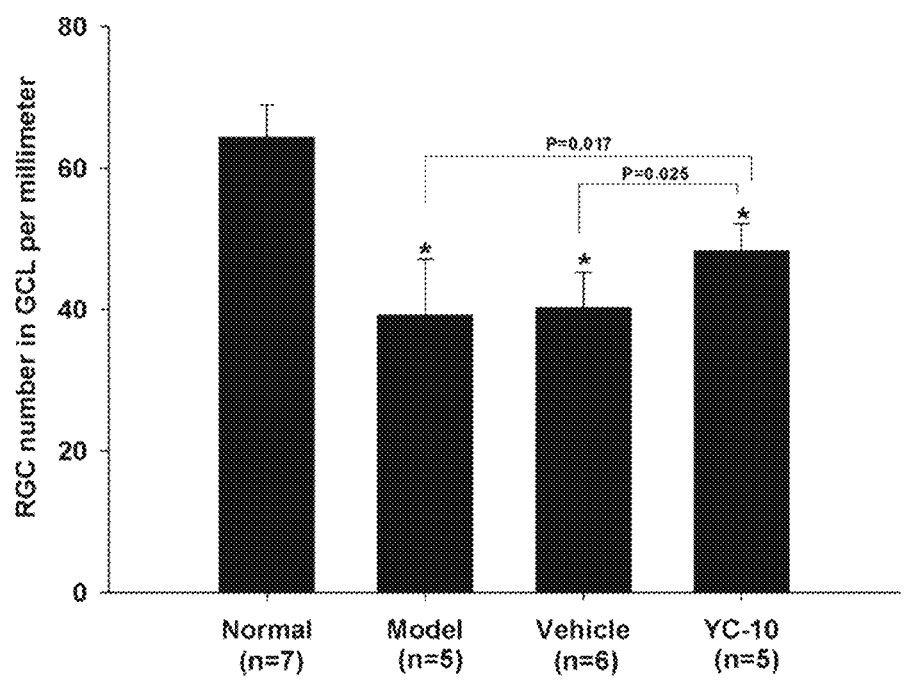
FIG. 8 a graph showing RGC statistics in different groups of samples in an eye high pressure and ischemia model.

As shown in FIG. 7, pathological examination showed that eye high pressure and ischemia can induce death of retinal ganglion cell (RGC). YC-10 was shown to reduce or prevent from ischemia-induced death, i.e., YC-10 can protect retinal ganglion cell from eye high pressure and ischemia-induced death. RGC counts in each group were recorded and reported in FIG. 8.

What is claimed is:

1. Compound 2β,3α,5α-trihydroxy-androst-6-one, having the structure of formula I:

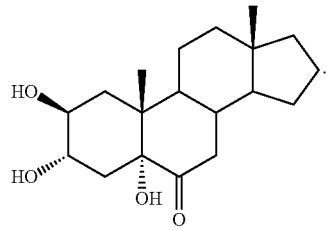

(Formula I)

2. A pharmaceutical composition, comprising a therapeutically effective amount of the compound of claim 1, and a pharmaceutically acceptable carrier.

3. The pharmaceutical composition of claim 1, further comprising a second neuron protective agent.

4. The pharmaceutical composition of claim 3, wherein the second neuron protective agent is a retinal ganglion cell protective agent.

5. The pharmaceutical composition of claim 1, further comprising a second anti-tumor drug.

6. A method for preparing the compound of claim 1, wherein the method comprises:
   (a) using androst-5-en-3-ol as starting material to obtain a compound VI, that is 3β-p-toluensulfonyloxy-5α-hydroxy-androst-6-one;
   (b) subjecting the compound VI to an elimination reaction to obtain compound IX, that is 5α-hydroxy-androst-2-en-6-one; and
   (c) subjecting the compound IX to oxidation at the 2-position double bond and hydrolysis to obtain the compound of claim 1.

* * * * *